United States Patent [19]

Abbott et al.

[11] Patent Number: 5,382,744
[45] Date of Patent: Jan. 17, 1995

[54] CONTROL OF SYNTHETIC ISOPENTANE PRODUCTION DURING ALKYLATION OF AMYLENES

[75] Inventors: Ronald G. Abbott, Kingwood, Tex.; Bruce B. Randolph; Richard L. Anderson, both of Bartlesville, Okla.

[73] Assignee: Phillips Petroleum Company, Bartlesville, Okla.

[21] Appl. No.: 88,942

[22] Filed: Jul. 12, 1993

[51] Int. Cl.$^6$ ............................ C07C 2/58; C07C 2/62
[52] U.S. Cl. .................................. 585/709; 585/723
[58] Field of Search ............... 585/709, 708, 331, 956, 585/723

[56] References Cited

U.S. PATENT DOCUMENTS 2,403,649 7/1946 Frey ................................. 260/683.5
2,662,103 12/1953 Matuszak ......................... 260/683.4
3,679,771 7/1972 Hutson, Jr. et al. ............. 260/676 R
4,262,155 4/1981 Hutson, Jr. ......................... 585/331
4,429,173 1/1984 Hutson, Jr. et al. ................ 585/331

OTHER PUBLICATIONS

Carberry, James J., *Chemical and Catalytic Reaction Engineering*, McGraw-Hill, Inc. (1976), pp. 39-42.

*Primary Examiner*—Asok Pal
*Assistant Examiner*—Bekir L. Yildirim
*Attorney, Agent, or Firm*—Charles W. Stewart

[57] ABSTRACT

A method of minimizing or controlling the production of synthetic isopentane during the catalyzed alkylation reaction of amylenes and isoparaffins by providing a concentration of isopentane in the alkylation reactor feed material.

9 Claims, No Drawings

CONTROL OF SYNTHETIC ISOPENTANE PRODUCTION DURING ALKYLATION OF AMYLENES

This invention relates generally to the alkylation of hydrocarbons. More specifically, however, the invention relates to the control or suppression of the production of synthetic isopentane during the alkylation of amylenes.

Recently promulgated federal regulations have placed new vapor pressure limitations on motor fuels resulting in the need to remove from gasoline certain quantities of lighter, relatively high vapor pressure components, such as, for example, butanes and isopentane. One problem, however, which results from the removal of such compounds from the gasoline pool is the need to find some other use for the butanes and isopentane. This is a particular problem with isopentane since it can be produced concurrently with the production of gasoline. Therefore, it is generally required for the butanes or isopentanes removed from gasoline to be consumed as a feedstock to certain other processes in order to eliminate the volume of such compounds in the gasoline pool.

A recent new concern that has arisen due to the new federal vapor pressure limitations placed on gasoline is the formation or production of synthetic isopentane during the hydrogen fluoride catalyzed alkylation of amylene olefin compounds. Traditionally, the production of synthetic isopentane has not been much of a concern; but, instead, it has been desirable because of the relatively high octane value of isopentane. However, due to the aforementioned regulatory changes, the commercial trend is now towards the removal of isopentane from the gasoline pool. It has been suggested by those skilled in the art, e.g. U.S. Pat. No. 4,429,173, that one means by which synthetic isopentane is removed from a product of a hydrogen fluoride catalyzed amylene alkylation process is to separate the isopentane, which can include synthetic isopentane, from the alkylate product and charge it to a separate dehydrogenation step to product olefins which can suitably be used as an alkylation process feed. While these additional process steps can effectively assist in the removal of isopentane contained in an alkylate product stream, they do not have numerous drawbacks. For instance, the separate dehydrogenation step requires additional capital to be invested in costly new equipment. Furthermore, there are operating costs associated with the dehydrogenation of isopentane. Finally, because of the separate and distinct process steps associated with the separation and dehydrogenation of isopentane contained in an alkylate product, it becomes difficult to control the net amount of isopentane produced synthetically during the alkylation reaction of amylenes.

Thus, it is an object of this invention to provide a method of controlling the amount of synthetic isopentane produced during the catalystic alkylation of amylenes.

A further object of this invention is to provide an alkylation process that has a suppressed ability to produce synthetic isopentane during the alkylation of amylene compounds.

A still further object of this invention is to provide an alkylation process that operates such that there is a net consumption of isopentane when amylenes are being alkylated.

The invention includes a method of controlling synthetic isopentane production during the alkylation of amylenes by isobutene. When language referring to amylene alkylation or the alkylation of amylenes is used herein, it shall means that amylene olefins are reacted with isobutane to nominally form a paraffin compound having nine carbon atoms. The first step of the inventive method includes contacting within a reaction zone a mixture where said mixture comprises amylenes and isobutane, with an alkylation catalyst. A reactor effluent is produced from the reaction zone and comprises an alkylate product and a synthetic isopentane product. Synthetic isopentane is controlled by adding a controlled amount of isopentane to said mixture in an amount effective for producing said desired amount of synthetic isopentane production.

Another embodiment of the invention is an alkylation process for the alkylation of amylenes by isoparaffins, wherein said alkylation process has a suppressed ability to produce synthetic isopentane. The first step of this process includes contacting within a reaction zone a mixture with an alkylation catalyst, said mixture comprising amylenes, isobutane, and isopentane in an amount that is effective for suppressing the production of synthetic isopentane. The contacting step is followed by recovering from said reaction zone a reaction zone product which comprises an alkylate product having a reduced concentration of synthetic isopentane below that which would result when said mixture, having substantially no isopentane concentration, is contacted with said alkylation catalyst.

A further embodiment of the invention is a method of suppressing the production of synthetic isopentane during the alkylation of amylenes by isobutane. The method includes contacting within a reaction zone a mixture of said amylenes and said isobutane with an alkylation catalyst and in the presence of a controlled amount of isopentane wherein said controlled amount of isopentane is such that the molar ratio of isopentane to amylene in said mixture exceeds 2 to 1 and producing a reaction zone effluent.

One of the important aspects of the inventive process is its ability to suppress, inhibit or eliminate the product of synthetic isopentane when amylenes are alkylated with isobutane in the presence of a hydrogen fluoride catalyst. A further important aspect of the process is its ability under certain precise process conditions to consume isopentane during the HF catalyzed alkylation reaction of amylenes with isobutane. In view of the ability of the process to suppress, inhibit or eliminate synthetic isopentane production and in certain circumstances to provide for isopentane consumption, a capability is provided for controlling, within certain limitations, the amount of isopentane that can be contained in an alkylation reaction effluent stream. Certain of the inventive process characteristics and attributes can be expressed or represented quantitatively by the selectivity or negative selectivity of the process toward the product of isopentane. The term "selectivity", as used herein, shall mean the ratio of the net synthetic isopentane produced to the amylene contained in the process feedstock. In the case where there is $iC_5$ consumption during the alkylation reaction, this may be referred to herein as "negative selectivity". The term "negative selectivity", shall mean the ratio of isopentane contained in a process feedstock that is consumed to the amylene contained in said feedstock.

As used herein, the term "synthetic isopentane" shall mean the net isopentane produced during a hydrogen fluoride catalyzed alkylation reaction of olefin compounds with isoparaffin compounds. Thus, the synthetic isopentane produced during an alkylation reaction step shall be the difference between the total mass of isopentane contained in an alkylate product effluent leaving an alkylation reaction zone and the total mass of isopentane contained in the feedstock to the alkylation reaction zone. It is theorized that the reaction mechanism by which synthetic isopentane is produced is the result of a hydrogen transfer reaction which is a chain initiated reaction in which tertiary butyl carbonium ions are formed and are involved in the chain reaction to form the ultimate products of isopentane and a paraffin hydrocarbon. One theorized mechanism for the hydrogen transfer reaction which occurs when amylene is alkylated with isobutane is as follows. See, Rosenwald, R. H., Kirk-Othemer Encyclopedia of Chemical Technology, 3rd Ed. (1978), 2, 50.

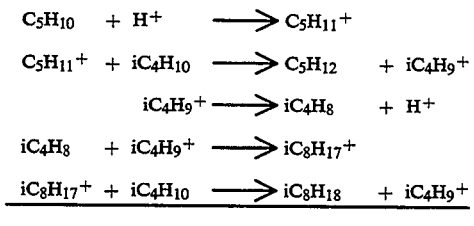

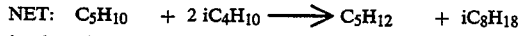

It is also theorized that certain of the physical phenomena relating to the features of inventive process can be attributed to various competing reactions which include the disproportionation reaction that involves the reaction of two intermediate molecules of a paraffin hydrocarbon compound each having an identical number of carbon atoms to form two separate paraffin hydrocarbon compounds one of which has fewer carbon atoms that the intermediate molecules and one of which has more carbon atoms than the intermediate molecules. One particularly important disproportionation reaction can be represented by the reaction formula as follows.

The inventive method is generally described as including the process step of contacting a feedstock with a catalyst within a reaction zone and producing, recovering or withdrawing a reaction zone product or effluent from the reaction zone. The feedstock can comprise a mixture of olefin hydrocarbons and isoparaffin hydrocarbons. The olefin hydrocarbons which can be used in the practice of the invention can include the monoolefins containing at least three carbon atoms per molecule. Presently preferred olefins for use in the practice of the invention are those monoolefins containing three to six carbon atoms per molecule. Thus, olefin hydrocarbons of the reactor feedstock mixture can include monoolefins selected from the group consisting of propene, butenes, pentenes, hexenes and mixtures of any two or more thereof. The isoparaffin hydrocarbons which can be used in the practice of the invention can include those having at least four carbon atoms per molecule and, preferably, the isoparaffins can be selected from the group consisting of isobutane, isopentane, and mixtures thereof.

It is one function of the inventive process or method to provide means for controlling the amount of synthetic isopentane produced during the catalyzed alkylation of amylenes by isobutane. As earlier described herein, during the hydrogen fluoride catalyzed alkylation of amylenes by isobutane, often, undesirable hydrogen transfer side reactions occur by which synthetic isopentane is produced. Isopentane has increasingly become an undesired gasoline component primarily because of its high volatility or high Reid vapor pressure as compared to other gasoline components having comparable octane values. Thus, it is desirable to remove by any suitable means isopentane from gasoline blending components such as an alkylation reaction product or alkylate or, in the case where there is a net isopentane production, it is desirable to inhibit, suppress or eliminate such synthetic isopentane production.

It has been discovered that if suitable proportions of isopentane are employed as a portion of an alkylation reaction zone feed mixture, which can also include amylenes and isobutane, the tendency of the alkylation reaction to produce synthetic isopentane is inhibited or suppressed. Thus, a controlled amount of isopentane can be added to an alkylation reaction zone feed mixture such that it is effective for suppressing the production of synthetic isopentane and for providing a reaction zone effluent product or alkylate having a reduced concentration of synthetic isopentane below that which would result when the alkylation reaction zone feed mixture, having substantially no isopentane concentration, is contacted with an alkylation catalyst within the alkylation reaction zone.

The weight ratio of isopentane to amylene in the alkylation reaction zone feed that has been found to be effective in suppressing the hydrogen transfer side reactions that produce synthetic isopentane generally can exceed about 1.5, but a more effective ratio is that which exceeds about 2.0. An upper limit for an effective ratio of isopentane to amylene in the alkylation reaction zone feed is primarily set by other factors relating to the ability of the process system to handle the additional volume of isopentane rather than by the inhibiting effect of the presence of the isopentane in the reaction zone or feed. Thus, the upper limit for the weight ratio of isopentane to amylene in the alkylation reaction zone feed is around 12:1 thereby giving a desired range for the ratio of isopentane to amylene in the reaction zone feed of from about 1.5:1 to 12:1 and preferably, from about 2:1 to about 11:1. A more preferred range for the ratio of isopentane to amylene in the alkylation reactor feed is from 2.5:1 to 10:1.

It has also been discovered that, within the aforementioned ratios of isopentane to amylene in an alkylation reaction zone feed, there is a certain ratio of isopentane to amylene which effectively provides for a net consumption of isopentane as determined by the difference in the mass of isopentane in the reaction zone effluent and the mass of isopentane in the reaction zone feed being a negative value. The weight ratio of isopentane to amylene found to provide for a net consumption of isopentane in the alkylation reaction is in the range of from about 4.5:1 to about 6.5:1. Preferably, the weight ratio of isopentane to amylene in the alkylation reaction zone feed necessary to provide a net consumption of isopentane is from about 5:1 to about 6:1 and, most preferably, it is from 5.2:1 to 5.8:1. Thus, within a certain broad range for the weight ratio of isopentane to amylene in an alkylation reaction zone feed, it has been found that synthetic isopentane production during the alkylation reaction is inhibited or suppressed as the given isopentane-to-amylene ratio is increased but only up to a given point where no synthetic isopentane is produced, above such ratio, a net reduction of isopentane is achieved.

Because of the above-described physical impact that the presence of isopentane has upon the alkylation of amylenes in an alkylation reaction zone, the benefit from having the ability to control the amount of synthetic isopentane contained in an amylene alkylate product can be controlled within certain broad ranges is achieved. Furthermore, when one considers an alkylation process in terms of its relationship with other refinery processes for the production of gasoline and gasoline components, isopentane that has previously been a component of a gasoline pool can potentially be removed therefrom and utilized as a feedstock to an alkylation process whereby it is consumed during the alkylation reaction.

If the appropriate amount of isopentane is contained in an alkylation zone feedstock or added to such feedstock, the amount of synthetic isopentane produced can be such that the amount of synthetic isopentane product contained in the reactor effluent is less than about 0.8:1 as determined by the ratio of the weight of synthetic isopentane product in the reactor effluent to the weight of amylenes in the alkylation reaction zone feed mixture. Preferably, the amount of isopentane contained in an alkylation reactor feed can be controlled such that the ratio of the weight of synthetic isopentane product to the weight of amylenes contained in the alkylation reaction zone feed mixture is less than about 0.6:1; but, preferably, it is less than 0.3:1.

The catalyst used in the process or method can be any compound, composition or material that suitably provides for the alkylation reaction of olefins with isoparaffins. The alkylation catalyst can be a liquid catalyst or a solid catalyst which is either supported or unsupported. Presently, commercial alkylation catalysts include sulfuric acid and hydrogen fluoride. The preferred alkylation catalyst of the present invention includes hydrogen fluoride which can be used in any form suitable for achieving the objectives of the inventive method or process. Of the suitable hydrogen fluoride catalysts, it is preferred for the acid to be in substantially anhydrous form, although small quantities of water can be present. The liquid hydrogen fluoride catalyst, when it is not in the substantially anhydrous form, can have water present in the range from about 0.1 weight percent to about 5 weight percent and, preferably, the water will be present in the range from 0.5 weight percent to 4 weight percent. It is preferred for the hydrofluoric acid catalyst to contain at least about 86 weight percent HF. Thus, a convenient and commercially practical range for the HF content of the catalyst is from 86 to 97 weight percent HF.

To improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. IT is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst generally should be sufficient to provide for essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40–90 volume percent catalyst phase and about 60–10 volume percent hydrocarbon phase, and wherein good contact of olefin with isoparaffin is maintained in the reaction zone, essentially complete conversion of olefin may be obtained at alkylation space velocities in the range of about 0.01 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.01 to about 200 (v/v/hr.) and allowing essentially complete conversion of olefin reactant in the alkylation zone.

In one embodiment of the alkylation process, the reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. A portion of the catalyst can continuously be regenerated or reactivated as described herein, or by any other suitable treatment, and returned to the alkylation reactor.

The following examples will serve to further illustrate the invention.

EXAMPLE I

The data presented in Example II were obtained using a 300 mL continuous stirred tank reactor (CSTR) with hydrocarbon feed rates of 600 mL per hour, using an HF catalyst containing approximately 7% acid soluble oils and 2% water. The temperature of the reactor contents were maintained at 90° F. while stirring at a rate of 2000 rpm. The acid recirculation rate was 700 mL/hour. Samples were taken at specified intervals and analyzed by gas chromatography. In cases where peak identity confirmation was required, gas chromatographic and mass spectral methods were employed.

EXAMPLE II

Shown in Table I are the data obtained from the alkylation of a feed containing a weight ratio of isobutane to 2-methyl-2-butene (2MB2) of 10:1. Shown are the isopentane selectivities at the indicated time intervals into the reaction and other information. The average selectivity of 2MB2 to form isopentane is 74.2 percent on a molar basis. This indicates that, on the average, approximately 74 mole percent of the 2MB2 fed into the reactor is converted to isopentane on a mole-to-mole basis. This can be an indication that relatively large concentration levels of $C_8$ material is produced via the hydrogen transfer mechanism. Table II presents the data from the more complete analyses of the alkylates corresponding those shown in Table I for the given time intervals into the reaction. These data suggest that the major products of the alkylation reaction are $C_8$ and $iC_5$.

Shown in Table III are data obtained from the alkylation of a feed containing a weight ratio of $iC_4/iC_5/2MB2$ of 13:5:1. It is significant that the isopentane selectivity has been reduced by approximately 80% over that of the Table I feed, which did not contain $iC_5$. Table IV presents the data from the more complete analyses of the alkylates corresponding to those shown in Table III for the given time intervals into the reaction. A comparison of the compositions of the alkylates presented in Table II with those of Table IV indicates that the concentrations of $C_6$ and $C_9+$ in the Table IV alkylates are significantly greater than those concentrations of the Table II alkylates while the concentrations of $C_8$ material are lower. The nearly doubled increase in production of $C_9+$ material can be attributed to the direct alkylation of amylene with isobutane. The increase in $C_6$ production is believed to be due to the disproportionation of $iC_5$ to 2- and 3-methyl pentanes. The comparison of the data shows that there is a dramatic impact upon isopentane selectivity that results from adding isopentane to an alkylation reactor feedstock. The hydrogen transfer reaction is believed to be suppressed by adding suitable quantities of $iC_5$ to an alkylation reactor feedstock as evidenced by the suppression of the production of synthetic isopentane and an increase in the production of $C_9+$ alkylate.

The data presented in Tables V and VI demonstrate that, at certain effective concentration levels of isopentane in an alkylation reactor feedstock, the hydrogen transfer reaction is suppressed to such an extent as to provide greater quantities of alkylation and disproportionation reaction products than that produced by having a lower concentration of $iC_5$ in the alkylation reactor feed. As shown in Table V, when there is an effective ratio of $iC_5$ to amylene in the alkylation reactor feedstock, a quantity of the $iC_5$ in the feedstock is actually consumed thereby providing a "negative selectivity" toward the production of $iC_5$.

Shown in Table V are data taken from the alkylation of a feed containing a weight ratio of $iC_5/2MB2$ of 10:1. On average, there is a net consumption of isopentane, or a "negative isopentane selectivity". This "negative isopentane selectivity" indicates the possibility that disproportionation of $iC_5$ to 2- and 3-methyl pentanes (and $iC_4$) is concurrently with the alkylation reaction. Table VI gives the results from a more complete analysis of the alkylates that correspond to those shown in Table V for the given time intervals into the reaction. A comparison of the $C_6$ and $C_9+$ concentrations presented in Tables II, IV and VI shows that both increase with an increasing ratio of isopentane to amylene in the alkylation reactor feed. This is most likely due to an increased disproportionation of $iC_5$ to $iC_4$ and methylpentanes. The amount of $C_8$ material in the alkylate is significantly below that which results when a lower $iC_5/2MB2$ feed ratio is utilized, indicating that the hydrogen transfer reaction is suppressed.

The data presented in Tables VII and VIII demonstrate the effect of having an $iC_4/iC_5$ ratio in the feeds of less than 1. In Table VII, the data indicate a very large, negative value for synthetic isopentane, which is indicative of enhanced $iC_5$ consumption. The $iC_5$ consumption is believed to be the result of disproportionation of $iC_5$ to methylpentanes and $iC_4$.

Table VIII presents the results of alkylate analyses that correspond to those shown in Table VII for the given time intervals into the reaction. A comparison of the data of Table VI with the data of Table VIII shows that the concentration of $C_9+$ materials in the alkylates are substantially the same, but the concentration of $C_6$ material in the alkylate of Table VIII is substantially greater than that of Table VI. This differential is believed to be due to the disproportionation of $iC_5$ to $iC_4$ and methylpentanes. The concentration of $C_8$ material in the alkylate of Table VIII is about 60% lower than that of the alkylate of Table VI, thus, indicating that an increasing $iC_5$ concentration in the alkylation reactor feedstock suppresses the hydrogen transfer reaction.

When alkylation reaction zone feeds contain more $iC_5$ than $iC_4$, there does not appear to be any gains in direct alkylation products, but an increased concentration of $iC_5$ above certain critical concentration levels result in a net reduction of $iC_5$ or, in other words, a net consumption of $iC_5$ due to competing disproportionation reactions.

TABLE I

| Determination of Isopentane Selectivity for $iC_4/2MB2$ Feed | | | | |
| --- | --- | --- | --- | --- |
| Time, hrs. | 2 | 4 | 6 | 8 |
| % Conversion 2MB2 | 100.0 | 100.0 | 100.0 | 100.0 |
| Feed Rate, (mL/hr) | 600 | 600 | 600 | 600 |
| g Feed/hr | 336 | 336 | 336 | 336 |
| Feed Composition | | | | |
| % Isobutane | 87.1 | 87.1 | 87.1 | 87.1 |
| % 2MB2 | 12.9 | 12.9 | 12.9 | 12.9 |
| Wt. Fraction 2MB2 Feed/hr | 0.129 | 0.129 | 0.129 | 0.129 |
| g 2MB2/hr | 43.3 | 43.3 | 43.3 | 43.3 |
| Moles 2MB2 Feed/hr | 0.618 | 0.618 | 0.618 | 0.618 |
| Product Analysis | | | | |
| % $iC_5$ in Product | 9.231 | 9.859 | 10.106 | 10.195 |
| g $iC_5$ Produced/hr | 31.016 | 33.126 | 33.96 | 34.26 |
| Moles $iC_5$ Produced/hr | 0.430 | 0.459 | 0.471 | 0.475 |
| Moles Synthetic $iC_5$ | 0.430 | 0.430 | 0.430 | 0.430 |

TABLE I-continued

Determination of Isopentane Selectivity for iC4/2MB2 Feed

| (per hour) | | | | |
|---|---|---|---|---|
| iC$_5$ Selectivity, (%) | | 69.6 | 74.3 | 76.2 | 76.8 |
| (Average) % | | 74.2 | | | |
| Ratio iC$_5$/2MB2 (Feed) | | 0 | | | |

TABLE II

Alkylate from iC4/2MB2 Feed

| TOS, hrs. | 2 | 4 | 6 | 8 | Average |
|---|---|---|---|---|---|
| % Conversion | 100.0 | 99.70 | 100.00 | 100.00 | 100.00 |
| Lights | 10.52 | 10.28 | 9.85 | 9.80 | 10.11 |
| C$_5$+ Material (on iC$_4$-Free Basis) | | | | | |
| iC$_5$ | 30.94 | 31.99 | 32.33 | 32.38 | 31.91 |
| nC$_5$ | 0.07 | 0.00 | 0.00 | 0.00 | 0.02 |
| C$_6$ | 2.38 | 2.16 | 2.23 | 2.25 | 2.26 |
| C$_7$ | 1.45 | 1.22 | 1.23 | 1.23 | 1.28 |
| C$_8$ | 45.79 | 45.73 | 45.69 | 45.87 | 45.77 |
| C$_9$+ | 8.85 | 8.62 | 8.69 | 8.43 | 8.65 |
| C$_6$+ Material (on iC$_4$/iC$_5$-Free Basis) | | | | | |
| nC$_5$ | 0.10 | 0.00 | 0.00 | 0.00 | 0.03 |
| C$_6$ | 3.45 | 3.18 | 3.30 | 3.33 | 3.32 |
| C$_7$ | 2.10 | 1.79 | 1.82 | 1.82 | 1.88 |
| C$_8$ | 66.30 | 67.24 | 67.52 | 67.83 | 67.22 |
| C$_9$+ | 12.81 | 12.67 | 12.84 | 12.47 | 12.70 |
| Lights | 15.23 | 15.12 | 14.56 | 14.49 | 14.85 |

Feed: 10/1 iC$_4$/2MB2
Lights = All material ≦C$_4$ except isobutane

TABLE III

Determination of Isopentane Selectivity for iC4/iC5/2MB2 Feed No. 1

| Time, hrs. | 2 | 4 | 6 | 8 |
|---|---|---|---|---|
| % Conversion 2MB2 | 99.48 | 99.29 | 99.53 | 99.47 |
| Feed Rate, (mL/hr) | 600 | 600 | 600 | 600 |
| g Feed/hr. | 336 | 336 | 336 | 336 |
| Feed Composition | | | | |
| % Isobutane | 68.14 | 68.14 | 68.14 | 68.14 |
| % Isopentane | 26.04 | 26.04 | 26.04 | 26.04 |
| % 2MB2 | 5.03 | 5.03 | 5.03 | 5.03 |
| Wt. % 2MB2/hr | 0.05 | 0.05 | 0.05 | 0.05 |
| g 2MB2/hr | 16.88 | 16.88 | 16.88 | 16.88 |
| Moles 2MB2 reacted/hr | 0.241 | 0.241 | 0.241 | 0.241 |
| g iC$_5$ added/hr | 87.5 | 87.5 | 87.5 | 87.5 |
| Moles iC$_5$ added/hr | 1.213 | 1.213 | 1.213 | 1.213 |
| Product Analysis | | | | |
| % iC$_5$ in Product/hr | 26.145 | 26.701 | 26.697 | 27.017 |
| g iC$_5$ in Product/hr | 87.85 | 89.71 | 89.70 | 90.78 |
| Moles iC$_5$ in Product/hr | 1.218 | 1.244 | 1.243 | 1.258 |
| Moles Synthetic iC$_5$/hr | 0.005 | 0.031 | 0.030 | 0.045 |
| iC$_5$ Selectivity (%) | 2.01% | 12.8% | 12.7% | 18.9% |
| Average (4–8 hrs) = 14.8% | | | | |
| Ratio iC$_5$/2MB2 (Feed) = 5.18 | | | | |

TABLE IV

Alkylate From iC4/iC5/2MB2 Feed No. 1

| TOS, hrs. | 2 | 4 | 6 | 8 | Average |
|---|---|---|---|---|---|
| % Conversion | 99.48 | 99.29 | 99.53 | 99.47 | 99.44 |
| Lights | 0.53 | 0.46 | 0.39 | 0.40 | 0.45 |
| C$_5$+ Material (on iC$_4$-Free Basis) | | | | | |
| iC$_5$ | 73.04 | 74.31 | 75.17 | 74.69 | 74.30 |
| nC$_5$ | 0.42 | 0.44 | 0.43 | 0.42 | 0.43 |
| C$_6$ | 2.74 | 2.46 | 2.44 | 2.45 | 2.52 |
| C$_7$ | 0.70 | 0.45 | 0.45 | 0.45 | 0.51 |
| C$_8$ | 14.39 | 15.24 | 14.98 | 15.21 | 14.96 |
| C$_9$+ | 8.21 | 6.64 | 6.14 | 6.42 | 6.85 |
| C$_6$+ Material (on iC$_4$/iC$_5$-Free Basis) | | | | | |
| nC$_5$ | 1.56 | 1.71 | 1.73 | 1.66 | 1.67 |
| C$_6$ | 10.16 | 9.58 | 9.83 | 9.68 | 9.81 |
| C$_7$ | 2.60 | 1.73 | 1.80 | 1.79 | 1.98 |
| C$_8$ | 53.38 | 59.32 | 60.33 | 60.09 | 58.28 |
| C$_9$+ | 30.45 | 25.85 | 24.73 | 25.37 | 26.60 |
| Lights | 1.96 | 1.71 | 1.43 | 1.48 | 1.65 |

Feed: 68.14% iC$_4$, 26.04% iC$_5$, 5.03% 2MB2
Lights = All material ≦C$_4$ except isobutane
iC$_5$/2MB2 Ratio (feed) = 5.18

TABLE V

Determination of Isopentane Selectivity for iC4/iC5/2MB2 Feed No. 2

| Time, hrs. | 2 | 4 | 6 | 8 |
|---|---|---|---|---|
| % Converted | 99.34 | 99.38 | 99.50 | 99.15 |
| Feed Rate, mL/hr | 600 | 600 | 600 | 600 |
| g Feed/hr | 336 | 336 | 336 | 336 |
| Feed Composition | | | | |
| % iC$_4$ | 52.57 | 52.57 | 52.57 | 52.57 |
| % iC$_5$ | 42.48 | 42.48 | 42.48 | 42.48 |
| % 2MB2 | 4.21 | 4.21 | 4.21 | 4.21 |
| Wt. % 2MB2/hr | 0.042 | 0.042 | 0.042 | 0.042 |
| g 2MB2/hr | 14.15 | 14.15 | 14.15 | 14.15 |
| Moles 2MB2 reacted/hr | 0.202 | 0.202 | 0.202 | 0.202 |
| g iC$_5$ added/hr | 142.7 | 142.7 | 142.7 | 142.7 |
| Moles iC$_5$ added/hr | 1.978 | 1.978 | 1.978 | 1.978 |
| Product Analysis | | | | |
| % iC$_5$ in Product/hr | 40.658 | 41.741 | 42.147 | 42.550 |
| g iC$_5$ in Product/hr | 136.6 | 140.2 | 141.6 | 143.0 |
| Moles iC$_5$ Produced/hr | 1.893 | 1.944 | 1.963 | 1.982 |
| Moles Synthetic iC$_5$/hr | −0.085 | −0.034 | −0.015 | −0.003 |
| iC$_5$ Selectivity (%) | −41.98 | −16.97 | −7.60 | −1.71 |
| Average (4–8 hrs) | −7.62 | | | |
| Ratio iC$_5$/2MB2 (Feed) | 10.09 | | | |

TABLE VI

Alkylate From iC4/iC5/2MB2 Feed No. 2

| TOS, hrs. | 2 | 4 | 6 | 8 | Average |
|---|---|---|---|---|---|
| % Conversion | 99.34 | 99.38 | 99.50 | 99.19 | 99.35 |
| Lights | 0.30 | 0.27 | 0.23 | 0.32 | 0.28 |
| C$_5$+ Material (on iC$_4$-Free Basis) | | | | | |
| iC$_5$ | 80.93 | 80.67 | 80.71 | 80.67 | 80.75 |
| nC$_5$ | 0.59 | 0.58 | 0.59 | 0.58 | 0.59 |
| C$_6$ | 4.21 | 4.34 | 4.42 | 4.45 | 4.36 |
| C$_7$ | 0.55 | 0.58 | 0.60 | 0.61 | 0.59 |
| C$_8$ | 7.13 | 6.76 | 6.67 | 6.71 | 6.82 |
| C$_9$+ | 6.30 | 6.79 | 6.78 | 6.65 | 6.63 |
| C$_6$+ Material (on iC$_4$/iC$_5$-Free Basis) | | | | | |
| nC$_5$ | 3.08 | 3.01 | 3.07 | 3.02 | 3.05 |
| C$_6$ | 22.07 | 22.47 | 22.91 | 23.02 | 22.62 |
| C$_7$ | 2.87 | 3.02 | 3.09 | 3.13 | 3.03 |
| C$_8$ | 37.37 | 34.98 | 34.59 | 34.74 | 35.42 |
| C$_9$+ | 33.05 | 35.14 | 35.16 | 34.41 | 34.44 |
| Lights | 1.59 | 1.39 | 1.18 | 1.68 | 1.46 |

Feed: 52.47% iC$_4$, 42.48% iC$_5$, 4.2% 2MB2
Lights = All material ≦C$_4$ except isobutane
iC$_5$/2MB2 Ratio (Feed) = 10.1

TABLE VII

Determination of Synthetic Isopentane Selectivity for iC4/iC5/2MB2 Feed No. 3

| Time, hrs. | 2 | 4 | 6 | 8 |
|---|---|---|---|---|
| % Conversion | 99.68 | 99.66 | 99.61 | 99.56 |
| Feed Rate, mL/hr | 600 | 600 | 600 | 600 |
| g Feed/hr | 336 | 336 | 336 | 336 |
| Feed Composition | | | | |
| % iC$_4$ | 33.16 | 33.16 | 33.16 | 33.16 |
| % iC$_5$ | 63.03 | 63.03 | 63.03 | 63.03 |
| % 2MB2 | 3.00 | 3.00 | 3.00 | 3.00 |
| Wt. % | 0.030 | 0.030 | 0.030 | 0.030 |

TABLE VII-continued

Determination of Synthetic Isopentane Selectivity for iC4/iC5/2MB2 Feed No. 3

| 2MB2/hr | | | | |
|---|---|---|---|---|
| g 2MB2/hr | 10.093 | 10.093 | 10.093 | 10.093 |
| Moles 2MB2/hr | 0.144 | 0.144 | 0.144 | 0.144 |
| g iC5 added/hr | 211.8 | 211.8 | 211.8 | 211.8 |
| Moles iC5 added/hr | 2.94 | 2.94 | 2.94 | 2.94 |
| Product Analysis | | | | |
| Wt. % iC5 in Product | 55.73 | 57.66 | 58.43 | 58.36 |
| g iC5 in Product | 187.3 | 193.7 | 196.3 | 196.1 |
| Moles iC5 in Product | 2.60 | 2.69 | 2.73 | 2.72 |
| Moles Synthetic iC5/hr | −0.34 | −0.25 | −0.21 | −0.22 |
| iC5 Selectivity (%) | −236.1 | −173.6 | −145.8 | −150.9 |
| Average (4–8 hrs) | 157.8 | | | |
| Ratio iC5/2MB2 (Feed) | 21.01 | | | |

TABLE VIII

Alkylate From iC4/iC5/2MB2 Feed No. 3

| TOS, hrs. | 2 | 4 | 6 | 8 | Average |
|---|---|---|---|---|---|
| % Conversion | 99.68 | 99.66 | 99.61 | 99.56 | 99.63 |
| Lights | 0.12 | 0.11 | 0.11 | 0.12 | 0.12 |
| C5+ Material (on iC4-Free Basis) | | | | | |
| iC5 | 84.29 | 85.03 | 84.80 | 85.14 | 84.82 |
| nC5 | 0.80 | 0.82 | 0.82 | 0.82 | 0.82 |
| C6 | 5.88 | 5.92 | 6.02 | 5.82 | 5.91 |
| C7 | 0.94 | 0.96 | 0.96 | 0.98 | 0.96 |
| C8 | 2.62 | 2.00 | 1.97 | 1.93 | 2.13 |
| C9+ | 5.36 | 5.16 | 5.32 | 5.19 | 5.26 |
| C6+ Material (on iC4/iC5-Free Basis) | | | | | |
| nC5 | 5.07 | 5.48 | 5.37 | 5.54 | 5.37 |
| C6 | 37.39 | 39.52 | 39.60 | 39.18 | 38.92 |
| C7 | 5.99 | 6.41 | 6.33 | 6.57 | 6.33 |
| C8 | 16.67 | 13.38 | 12.97 | 13.00 | 14.01 |
| C9+ | 34.13 | 34.48 | 34.98 | 34.90 | 34.62 |
| Lights | 0.76 | 0.73 | 0.74 | 0.81 | 0.76 |

Feed: 33.16% iC4, 63.03% iC5, 3.00% 2MB2
Lights = All material ≦C4 except isobutane
iC5/2MB2 Ratio (Feed) = 21.01

EXAMPLE III

The data presented in Example IV were obtained using a 300 mL riser-type reactor with the feeds sprayed into a non-circulated layer of catalyst (300 ml). The feed rates were 300 mL per hour throughout the experimental run, and the temperature was held constant at 90° F. (±3° F.). The catalyst was composed of 92% HF, 2% water, and 6% acid soluble oils generated by the addition of pure 2-butenes to the HF/water catalyst mixture. Samples were taken at different times on stream and analyzed as described above.

EXAMPLE IV

Table IX presents the data resulting from the alkylation of a feed containing of 64.6% iC4, 29.2% iC5, and 5.4% 2MB2. Comparing these data to that of a similar feed presented in Table III, it is immediately apparent that a much high level of iC5 consumption is achieved. This is evidenced by the large, negative values for isopentane selectivity. In contrast, the alkylation of a feed containing a ratio of iC5 to 2MB2 of 5.18 in a CSTR reactor led to an average value for iC5 selectivities of 14.8%.

Table X presents further data from the analyses of alkylates presented in Table IX. A comparison of these results with those in Table IV indicates that the concentration levels of C6 material in the alkylates are similar. However, the amounts of C8 and C9+ material are reversed relative to Table IV data. These data indicate a possibility of a suppressed hydrogen transfer reaction since the amount of C8 material in the alkylate is reduced. The concentration of C9+ material in the alkylates indicates that the direct alkylation reaction is favored under these conditions. Some of these differences can be explained by the differences in contact time of hydrocarbon with the acid between the CSTR and the riser-reactor. In the CSTR, the contact time is on the order of several minutes greater than the hydrocarbon residence time within the riser reactor. These data suggest that short residence times may favor production of direct alkylation products and that longer residence times may allow for the disproportionation reaction to proceed to a greater degree. The data presented in Tables IX and IV illustrate that as the residence time is shortened, the extent of disproportionation is reduced.

TABLE IX

Determination of iC5 Selectivity for iC4/iC5/2MB2 Feed No. 4 (Riser Reactor)

| Time, hrs. | 2 | 4 | 6 | 10 |
|---|---|---|---|---|
| % Conversion | 100.0 | 100.0 | 100.0 | 100.0 |
| Feed Rate, mL/hr | 300 | 300 | 300 | 300 |
| g Feed/hr | 171.3 | 171.3 | 171.3 | 171.3 |
| Feed Composition | | | | |
| % iC4 | 64.62 | 64.62 | 64.62 | 64.62 |
| % iC5 | 29.24 | 29.24 | 29.24 | 29.24 |
| % 2MB2 | 5.366 | 5.366 | 5.366 | 5.366 |
| Wt. Fraction 2MB2/hr | 0.0537 | 0.0537 | 0.0537 | 0.0537 |
| g 2MB2/hr | 9.192 | 9.192 | 9.192 | 9.192 |
| Moles 2MB2/hr | 0.131 | 0.131 | 0.131 | 0.131 |
| g iC5 added/hr | 50.09 | 50.09 | 50.09 | 50.09 |
| Moles iC5 added/hr | 0.696 | 0.696 | 0.696 | 0.696 |
| Product Analysis | | | | |
| g iC5 in Product | 46.445 | 49.456 | 43.932 | 47.51 |
| % iC5 in Product | 27.113 | 28.871 | 25.646 | 27.736 |
| Moles iC5 in Product | 0.644 | 0.685 | 0.609 | 0.659 |
| Moles Synthetic iC5 | −0.052 | −0.011 | −0.087 | −0.037 |
| iC5 Selectivity (%) | −39.7 | −8.39 | −66.4 | −28.24 |
| Average (2–10 hrs.) | −35.7 | | | |
| Ratio iC5/2MB2 (Feed) | 5.6 | | | |

TABLE X

Alkylate From iC4/iC5/2MB2 Feed No. 4 (Riser Reactor)

| TOS, hrs. | 2 | 4 | 6 | 8 |
|---|---|---|---|---|
| % Conversion | 100.00 | 100.00 | 100.00 | 100.00 |
| Lights | 0.62 | 0.36 | 1.88 | 3.67 |
| C5+ Material (on iC4-Free Basis) | | | | |
| iC5 | 62.45 | 62.40 | 64.56 | 45.00 |
| nC5 | 0.30 | 0.31 | 0.32 | 0.26 |
| C6 | 3.18 | 3.19 | 3.17 | 2.71 |
| C7 | 1.49 | 1.48 | 1.24 | 1.77 |
| C8 | 13.74 | 16.79 | 13.67 | 23.72 |
| C9+ | 17.46 | 15.36 | 14.92 | 22.87 |
| C6+ Material (on iC4/iC5-Free Basis) | | | | |
| nC5 | 0.80 | 0.82 | 0.89 | 0.47 |
| C6 | 8.47 | 8.48 | 8.95 | 4.93 |
| C7 | 3.97 | 3.94 | 3.49 | 3.22 |
| C8 | 36.57 | 44.65 | 38.56 | 43.12 |
| C9+ | 46.48 | 40.84 | 42.10 | 41.58 |

TABLE X-continued

| Alkylate From iC$_4$/iC$_5$/2MB2 Feed No. 4 (Riser Reactor) | | | | |
|---|---|---|---|---|
| Lights | 1.65 | 0.95 | 5.29 | 6.68 |

Feed: 64.62% iC$_4$, 29.24% iC$_5$, 52.7% 2MB2
Lights = All material ≦C$_4$ except isobutane While certain embodiments of the invention have been described for illustrative purposes, the invention is not limited thereto. Various other modifications or embodiments of the invention will be apparent to those skilled in the art in view of this disclosure. Such modification or embodiments are within the spirit and scope of the disclosure.

What is claimed is:

1. A method for alkylating amylenes by isobutane thereby controlling synthetic isopentane production, said method comprises the steps of:
    contacting within a reaction zone a mixture, comprising amylenes and isobutane, with an alkylation catalyst;
    adding isopentane to said mixture in a controlled amount in the range of from about 2:1 to about 10:1 as determined by the ratio of the weight of said controlled amount of isopentane added to the said mixture to the weight of said amylenes in said mixture, thereby producing an amount of synthetic isopentane of less than about 0.8:1 as determined by the ratio of the weight of said synthetic isopentane to the weight of said amylenes in said mixture; and
    producing a reactor effluent from said reaction zone which comprises an alkylate product and a synthetic isopentane product.

2. A method as recited in claim 1, wherein the weight ratio of isobutane to amylenes in said mixture exceeds 2:1.

3. A method as recited in claim 2, wherein said alkylation catalyst comprises hydrogen fluoride.

4. An alkylation process for the alkylation of amylenes by isobutane, said alkylation process having a suppressed ability to produce synthetic isopentane, comprising the steps of:
    contacting within a reaction zone a mixture with an alkylation catalyst, said mixture comprising amylenes, isobutane and isopentane wherein the isopentane is present in said mixture in the range of from about 2:1 to about 10:1 as determined by the ratio of the weight of isopentane to the weight of amylenes in said mixture; and
    withdrawing a reactor effluent from said reaction zone which comprises an alkylate product and a synthetic isopentane product wherein the amount of said synthetic isopentane produce in said reactor effluent is less than about 0.8:1 as determined by the ratio of the weight of said synthetic isopentane product to the weight of amylenes in said mixture.

5. An alkylation process as recited in claim 4, wherein the weight ratio of isobutane to amylenes in said mixture exceeds 2:1.

6. An alkylation process as recited in claim 5, wherein said alkylation catalyst comprises hydrogen fluoride.

7. A method of suppressing the production of synthetic isopentane during the alkylation of amylenes by isobutane, said method comprises:
    contacting within a reaction zone a mixture of said amylenes and said isobutane with an alkylation catalyst and in the presence of a controlled amount of isopentane wherein said controlled amount of isopentane is such that the weight ratio of isopentane to amylene in said mixture exceeds 2 to 1; and
    producing a reaction zone effluent.

8. A method as recited in claim 7, wherein the weight ratio of isobutane to amylenes in said mixture exceeds 2:1.

9. A method as recited in claim 8, wherein said alkylation catalyst comprises hydrogen fluoride.

* * * * *

UNITED STATES PATENT AND TRADEMARK OFFICE
CERTIFICATE OF CORRECTION

PATENT NO.   : 5,382,744

DATED        : 1/17/95

INVENTOR(S)  : Ronald G. Abbott et al

It is certified that error appears in the above-identified patent and that said Letters Patent is hereby corrected as shown below:

Claim 4, column 14, line 15, delete "produce" and insert therefor
--- product ---.

Signed and Sealed this

Thirtieth Day of May, 1995

*Attest:*

BRUCE LEHMAN

*Attesting Officer*    *Commissioner of Patents and Trademarks*